US 7,857,787 B2

(12) United States Patent
Masters et al.

(10) Patent No.: US 7,857,787 B2
(45) Date of Patent: Dec. 28, 2010

(54) SYSTEMS AND METHODS FOR LOCKING AND DETECTING THE PRESENCE OF A CATHETER

(75) Inventors: Donald Masters, Fremont, CA (US); Scott Harshman, Kirkland, WA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 739 days.

(21) Appl. No.: 11/559,104

(22) Filed: Nov. 13, 2006

(65) Prior Publication Data

US 2007/0179473 A1 Aug. 2, 2007

Related U.S. Application Data

(60) Provisional application No. 60/735,805, filed on Nov. 12, 2005.

(51) Int. Cl.
*A61M 29/00* (2006.01)
*A61F 7/12* (2006.01)
*A61M 1/00* (2006.01)

(52) U.S. Cl. .................. 604/108; 604/153; 604/113
(58) Field of Classification Search ............. 604/108, 604/113; 285/330; 324/207
See application file for complete search history.

(56) References Cited

U.S. PATENT DOCUMENTS

| 4,378,212 A | 3/1983 | Waldron |
| 4,394,862 A * | 7/1983 | Shim ........................... 604/67 |
| 4,550,715 A | 11/1985 | Santangelo et al. |
| 4,669,465 A | 6/1987 | Moore et al. |
| 5,113,467 A | 5/1992 | Peterson et al. |
| 5,176,618 A * | 1/1993 | Freedman ..................... 600/12 |
| 5,626,129 A | 5/1997 | Klimm |
| 5,935,106 A * | 8/1999 | Olsen .......................... 604/153 |
| 6,126,681 A * | 10/2000 | Van Duren et al. ............ 607/96 |
| 6,201,388 B1 | 3/2001 | Pecheny et al. |
| 6,402,207 B1 | 6/2002 | Segal et al. |
| 6,612,624 B1 | 9/2003 | Segal et al. |
| 6,758,818 B2 | 7/2004 | Pantages et al. |
| 2001/0000832 A1 * | 5/2001 | Newman ...................... 29/714 |
| 2005/0015075 A1 | 1/2005 | Wright |
| 2005/0256451 A1 * | 11/2005 | Adams et al. ............. 604/93.01 |
| 2006/0079765 A1 * | 4/2006 | Neer et al. ................... 600/432 |
| 2006/0122576 A1 * | 6/2006 | Raja et al. ................. 604/890.1 |
| 2007/0250005 A1 * | 10/2007 | Fago et al. .................. 604/113 |

FOREIGN PATENT DOCUMENTS

| EP | 1709986 A | 10/2006 |
| JP | 11276488 | 10/1999 |

* cited by examiner

*Primary Examiner*—Nicholas D Lucchesi
*Assistant Examiner*—Ian K Holloway
(74) *Attorney, Agent, or Firm*—Frommer Lawrence & Haug LLP; Bruce E. Black

(57) ABSTRACT

The present invention provides systems and methods for locking and detecting the presence of a catheter. In an embodiment, a catheter system comprises a catheter and a magnet attached to a proximal end of the catheter. The catheter system further comprises a lock receptacle configured to receive and lock the proximal end of the catheter therein, and a Hall-effect sensor configured to detect the presence of the magnet, and hence the catheter, when the catheter is locked in the lock receptacle.

20 Claims, 10 Drawing Sheets

SYSTEMS AND METHODS FOR LOCKING AND DETECTING THE PRESENCE OF A CATHETER

RELATED APPLICATIONS

This application claims the benefit of U.S. Provisional Application Ser. No. 60/735,805 filed on Nov. 12, 2005.

FIELD OF INVENTION

The present invention relates generally to catheters, and more particularly to systems and methods for locking and detecting the presence of a catheter.

BACKGROUND

Catheters are used to gain access inside a patient's body to perform diagnosis and treatments within the body, e.g., by inserting the catheter through a blood vessel. Many catheter imaging systems use a rotating imaging transducer within the catheter to obtain images within the patient's body. Typically, the imaging transducer is attached to the distal end of a drive cable that extends through a lumen of the catheter. The proximal end of the drive cable is detachably connectable to a motor within a motor drive unit for rotating the drive cable and the imaging transducer. In operation, it is desirable to verify that the catheter is properly locked to the motor drive unit before the motor can be turned on to avoid damage to the catheter or a injury to a person inserting his/her finger in the motor drive unit.

Therefore, there is a need for systems and methods for locking and detecting the presence of a catheter.

SUMMARY OF INVENTION

The present invention provides systems and methods for locking and detecting the presence of a catheter.

In an embodiment, a catheter system comprises a catheter and a magnet attached to a proximal end of the catheter. The catheter system further comprises a lock receptacle configured to receive and lock the proximal end of the catheter therein, and a Hall-effect sensor configured to detect the presence of the magnet, and hence the catheter, when the catheter is locked in the lock receptacle.

In another embodiment, the lock receptacle is attached to a motor drive unit to lock the catheter to the motor drive unit and detect when the catheter is connected to the motor drive unit. In this embodiment, the Hall-effect sensor may be coupled to protection circuitry to disable the motor within the motor drive unit when the presence of the catheter is not detected.

In another embodiment, the magnet is attached to an indexing pin extending radially from the proximal end of the catheter. The lock receptacle comprises a radial groove configured to receive the indexing pin therein, and a plunger extending from a side wall of the radial groove, wherein the plunger is configured to lock the indexing pin between the plunger and a retaining wall of the radial groove. The catheter is locked in the lock receptacle by inserting the indexing pin into the radial groove of the lock receptacle, and rotating the catheter until the indexing pin is locked in place between the plunger and the retaining wall.

In another embodiment, multiple magnets can be placed at different positions on the catheter to enable the recognition of different catheters.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

DETAILED DESCRIPTION

Figure 1:
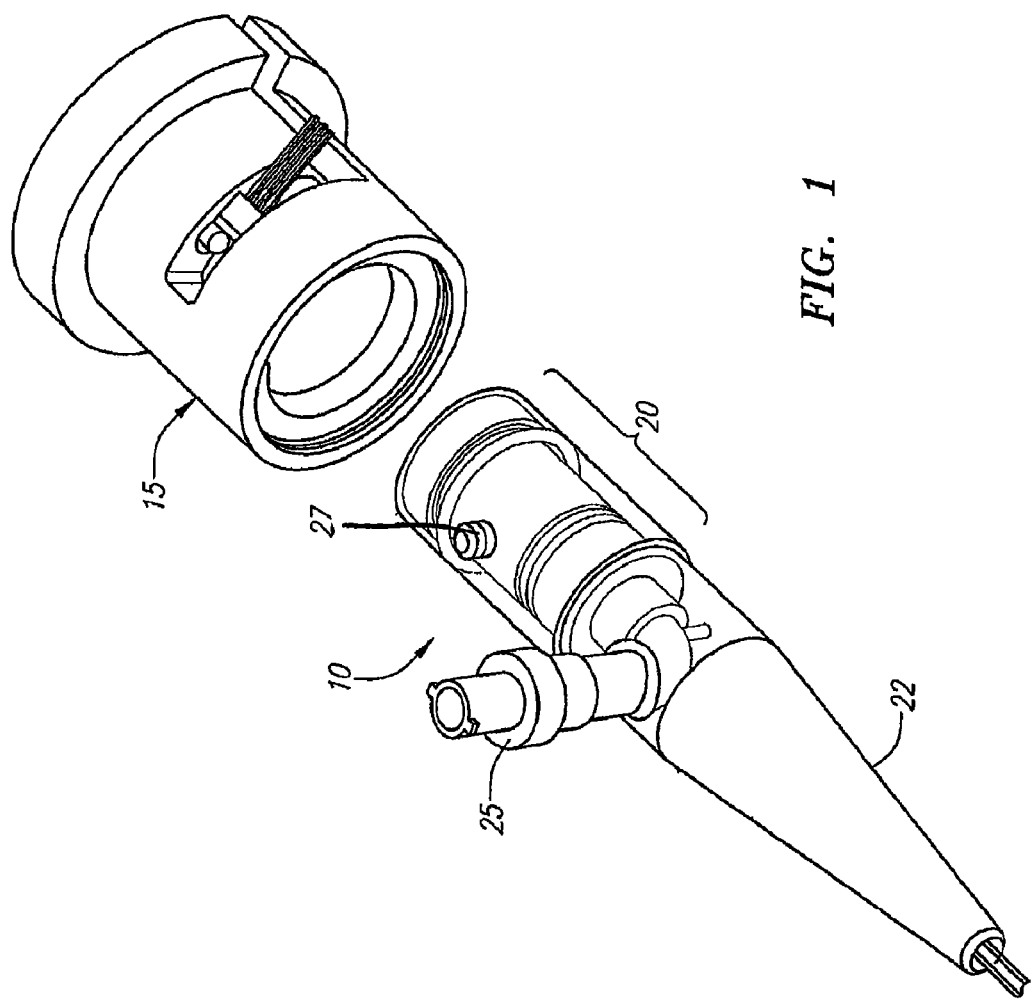
FIG. 1 is a perspective view of the proximal end of a catheter and a lock receptacle according to an embodiment.

FIG. 1 shows a perspective view of catheter 10 and a twist lock receptacle 15 according to an embodiment of the invention. The lock receptacle 15 is mounted to a motor drive unit (not shown) and is used for locking the proximal end of the catheter 10 to the motor drive unit. Motor drive units are well known in the art for driving a drive cable inside the catheter, and therefore a detailed description of a drive motor unit is not necessary for an understanding of the invention.

The proximal end of the catheter 10 comprises a hub 20 which locks into the lock receptacle 15, a cone-shaped strain relief 22, and a valve 25. The strain relief 22 is used to relieve strain caused by a user pulling the catheter to one side. The valve 25 is for injecting fluid, e.g., saline, into the catheter 10. The proximal end of the catheter 10 further comprises an index pin 27 extending outwardly from the hub 20. The index pin 27 and the hub 20 may be made of polycarbonate or other type of plastic. The index pin 27 may be a separate piece attached to the hub 20 by an adhesive. To better secure the index pin 27 to the hub 20, the index pin 27 may be coated with epoxy and inserted into a recess in the hub 20. Alternatively, the index pin 27 may be molded into the hub 20.

Figure 2:
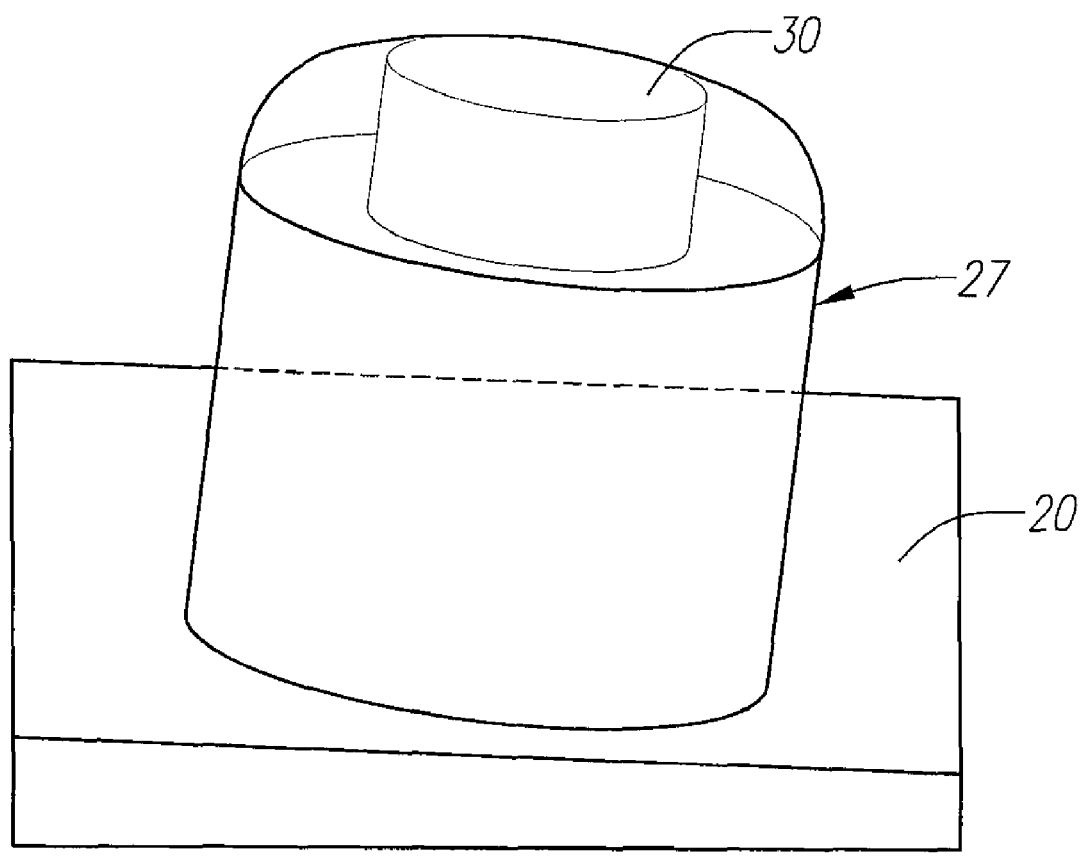
FIG. 2 is a blowup view of an indexing pin according to an embodiment.

FIG. 2 shows a blowup view of the index pin 27. The catheter 10 further comprises a magnet indicator 30 mounted to the top of the index pin 27. The magnet 30 may be a Neodymium magnet. The magnet 30 may be glued to the index pin 27, e.g., using a UV cured adhesive. The magnet 30 may be encapsulated in the glue. The magnet 30 works in conjunction with a Hall-effect sensor for detecting the catheter 10 in the locked position in the lock receptacle 15, as explained further below.

Figure 3:
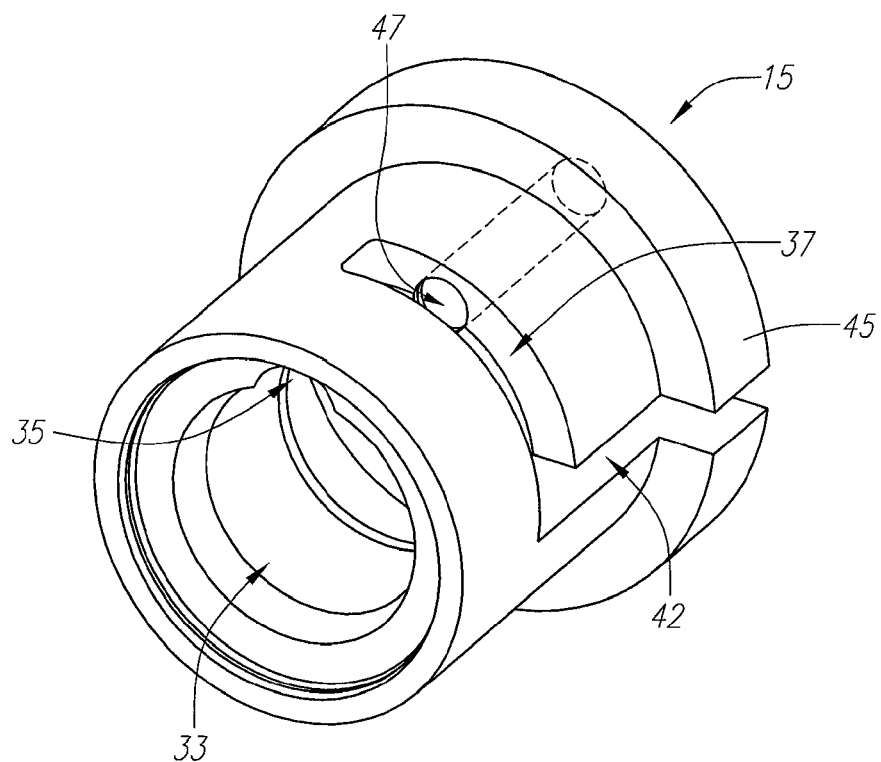
FIG. 3 is a prospective view of the lock receptacle according to an embodiment.
Figure 4:
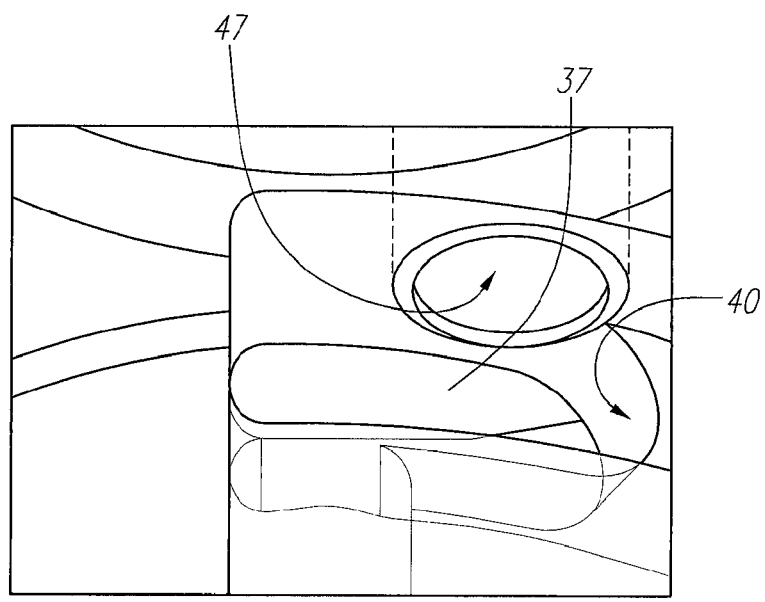
FIG. 4 is a blowup view of a retaining wall of the lock receptacle according to an embodiment.

FIG. 3 shows a perspective view of the lock receptacle 15, which preferably comprises of non-conductive materials, such as plastic or Polyetheretherketones ("PEEK"). The lock receptacle 15 has an inner cavity 33 for receiving the catheter hub 20. In FIG. 3, the inner cavity 33 is cylindrical to match the cylindrical shape of the hub 20. The lock receptacle 15 also has an internal axial groove 35 cut or etched into the inner cavity 33. The internal axial groove 35 is dimensioned to allow the indexing pin 27 of the hub 20 of the catheter 10 to pass through. The lock receptacle 15 also has an radial slot 37 connected at one end to the axial groove 35. FIG. 4 shows a close up of the radial slot 37. The radial slot 37 has an internal circular retaining wall 40. The retaining wall 40 is used to retain the indexing pin 27 when the hub 20 of the catheter 10 is inserted into the lock receptacle 15 such that the indexing pin reaches the radial slot 37 and rotated such that the indexing pin 27 reaches the retaining wall 40. The radial slot 37 further includes a plunger hole 47, having a plunger 49 that holds the indexing pin 27 and thus the catheter 10 in place. The locking receptacle 15 further includes an external axial slot 42, which is configured to receive and lock in place a Hall-effect sensor as will be explained below. The back of lock entry 45 to the external axial slot 42 is defined at the proximal end of the receptacle 15.

Figure 5:
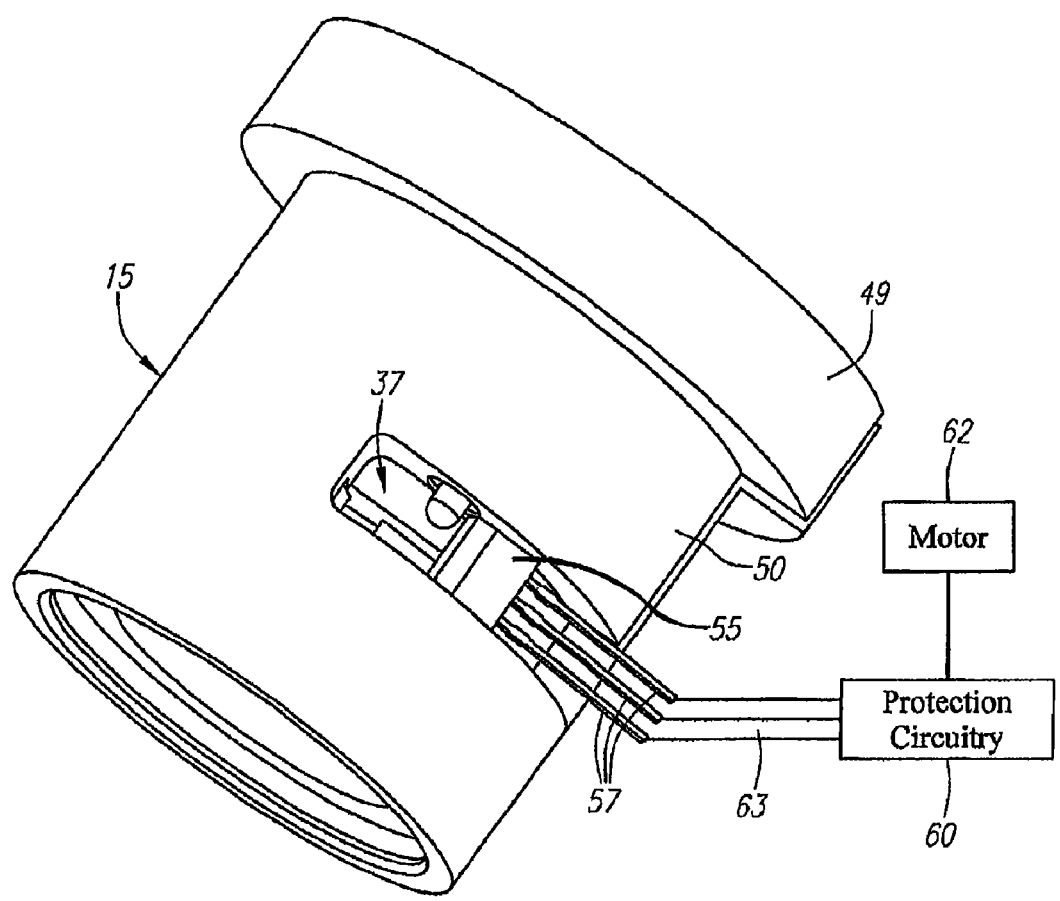
FIG. 5 is a blowup view of the lock receptacle with a Hall-effect sensor and a plunger according to an embodiment.

FIG. 5 shows a blowup view of the lock receptacle 15. In FIG. 5, a spring-loaded ball plunger 49 is inserted in the plunger hole 47. The plunger 49 has a ball-shaped end 50. Also shown is a Hall-effect sensor 55 inserted in the radial slot 37 via the external axial slot 42. Although the radial slot 37 is shown exposed for ease of illustration, it is to be understood that the slot 37 is enclosed. Preferably, the Hall-effect sensor 55 is secured in the radial slot 37 by an adhesive. The adhesive preferably encapsulates the Hall-effect sensor 55 to electrically isolate and/or seal the sensor 55. The Hall-effect sensor 55 is used to detect the presence of the magnet 30 of the indexing pin 27. Also shown are electrical leads 57 extending from the Hall-effect sensor 55. Although the leads 57 are shown as being straight in FIG. 5, the leads 57 are preferably bent to run inside the radial slot 37. Preferably, the leads 57 are encapsulated in a nonconductive material, e.g., adhesive used, to electrically isolate and/or seal the leads 57 from fluid leakage inside the lock receptacle 15. The Hall-effect sensor 55 is connected to a patient protection circuitry 60 that shuts off the motor 62 of the motor drive unit when the catheter 10 is not locked into the lock receptacle 15, as explained further below. The axial slot 42 may be used for running wires 63 therethrough from the leads 57 to the protection circuitry 60. Alternatively, the wires 63 may be inserted through a hole (not shown) that runs axially through the receptacle 15. The Hall-effect sensor 55 is positioned to be above the magnet 30 of the indexing pin 27 when the catheter 10 is locked into the lock receptacle 15. In this embodiment, two of the three leads 57 are used to provide voltage, e.g., 5 volts, and ground to the Hall-effect sensor 55 and the third lead is used to transmit the magnetic detection signal of the Hall-effect sensor 55.

Figure 6:
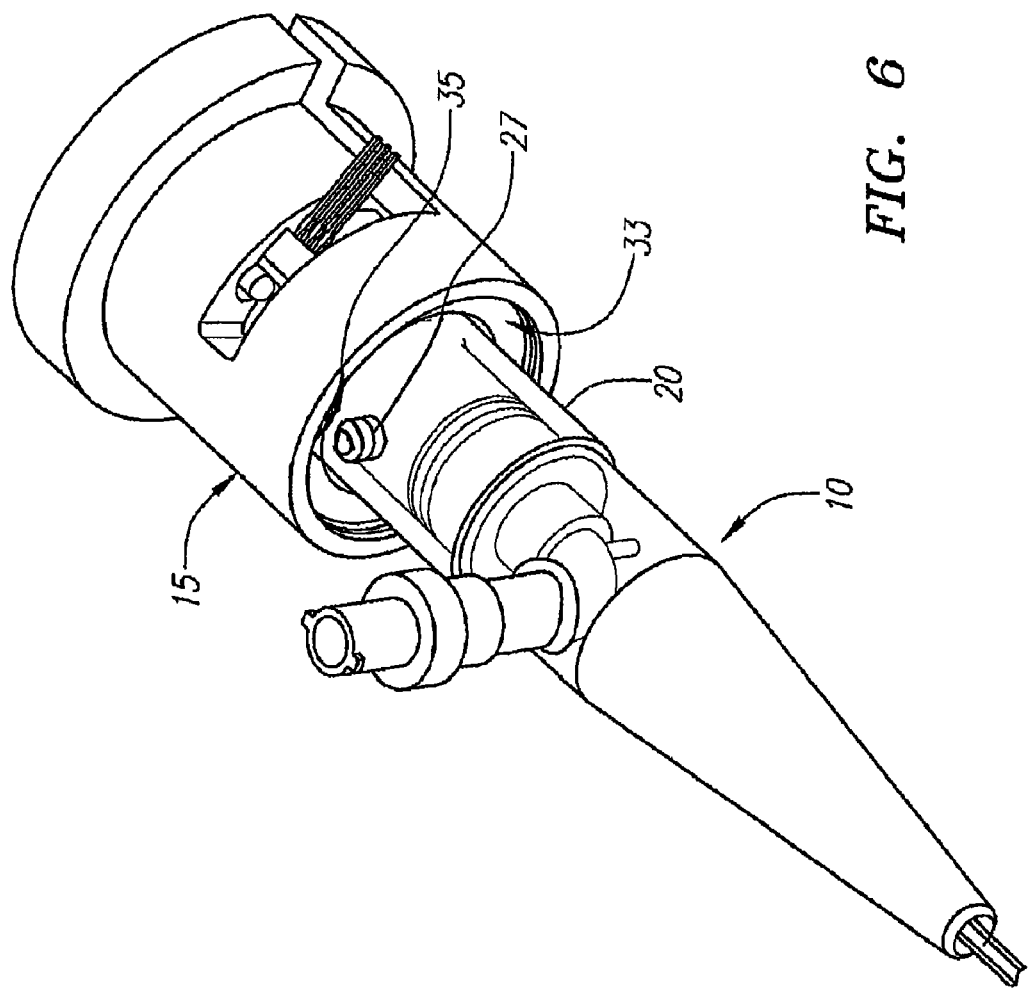
FIG. 6 is a prospective view of the catheter and the lock receptacle with the indexing pin aligned with an axial groove of the lock receptacle according to an embodiment.
Figure 7:
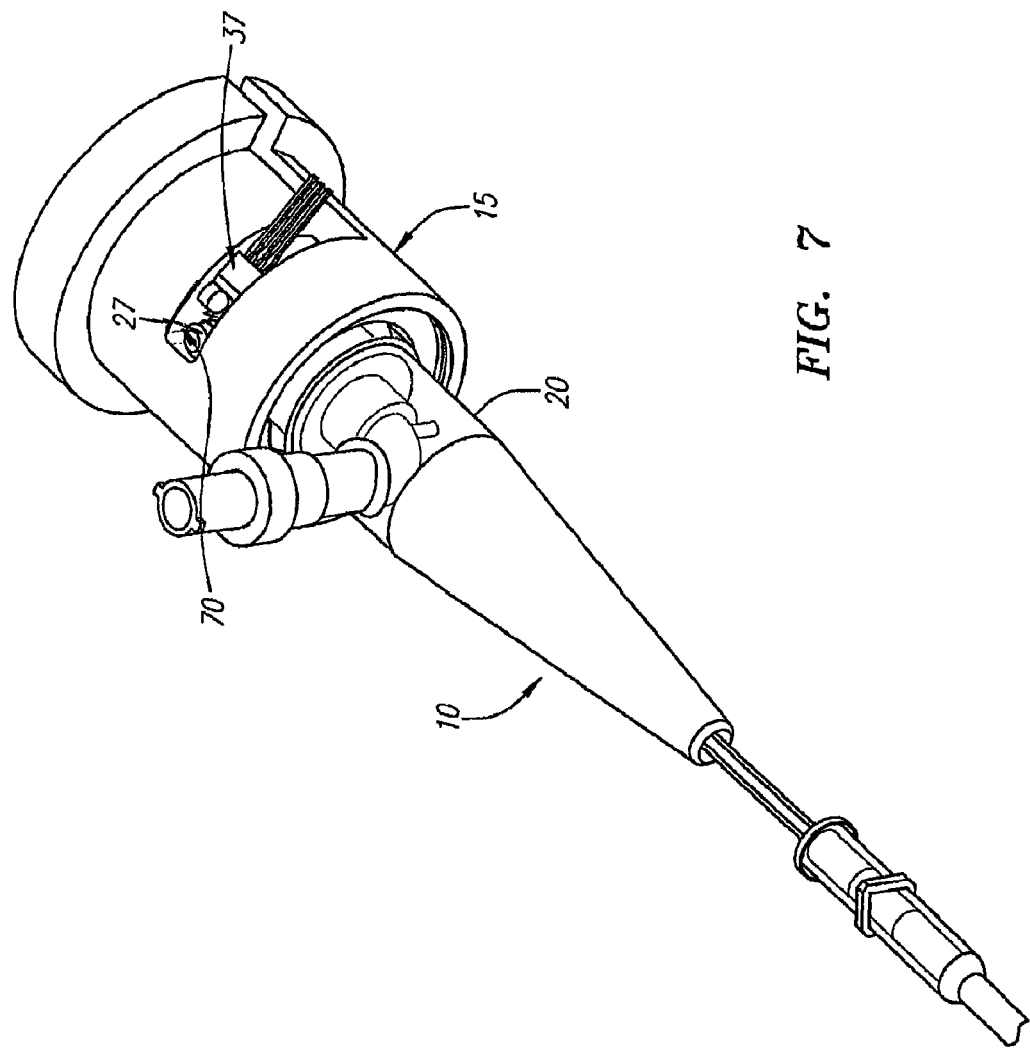
FIG. 7 is a prospective view of the catheter inserted into the lock receptacle according to an embodiment.

To lock the catheter 10 into the locking receptacle 15, the indexing pin 27 is aligned with the axial groove 35, as shown in FIG. 6. The catheter hub 20 is then inserted into the inner cavity 33 of the lock receptacle 15. As the catheter hub 20 is inserted into the inner cavity 33, the indexing pin 27 passes through the axial grove 35 running along the inner cavity 33. When the indexing pin 27 reaches the radial slot 37, the indexing pin 27 contacts a side wall 70 of the radial slot 37 as shown in FIG. 7. The side wall 70 prevents further axial movement of the catheter hub 20.

Figure 8:
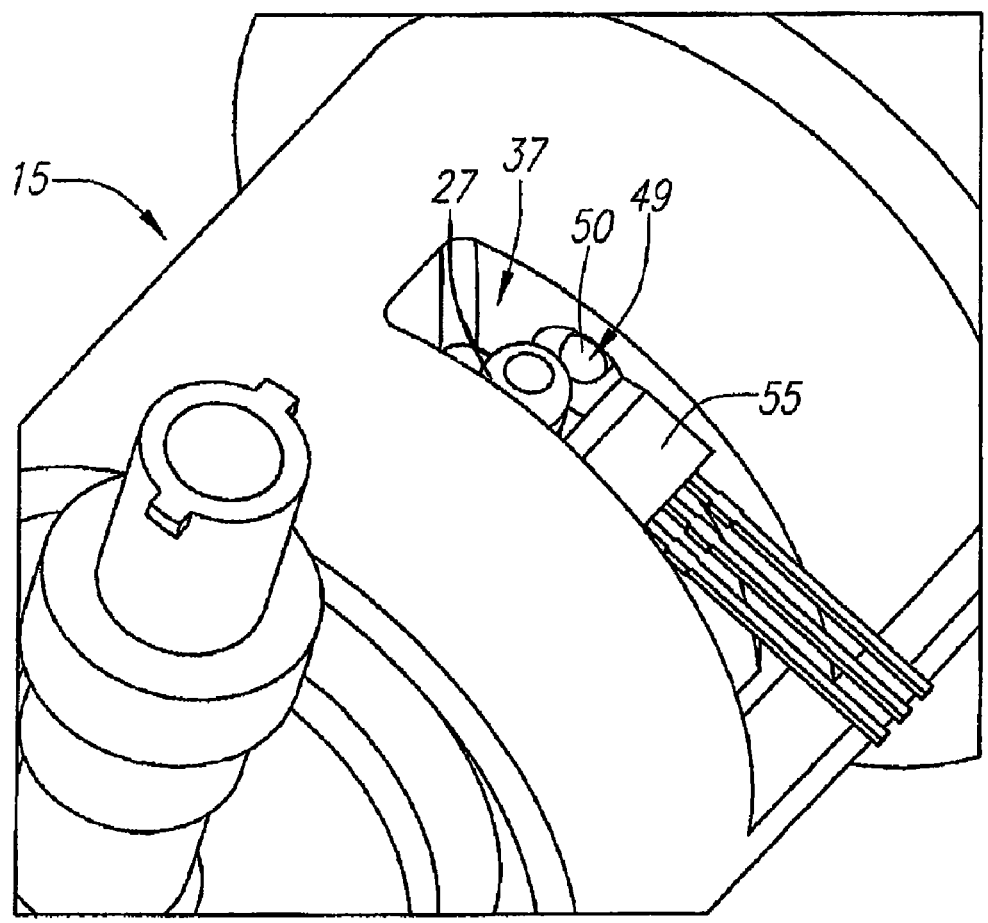
FIG. 8 is a blowup view of the catheter turned clockwise in the lock receptacle so that the indexing pin contacts the plunger of the lock receptacle according to an embodiment.
Figure 9:
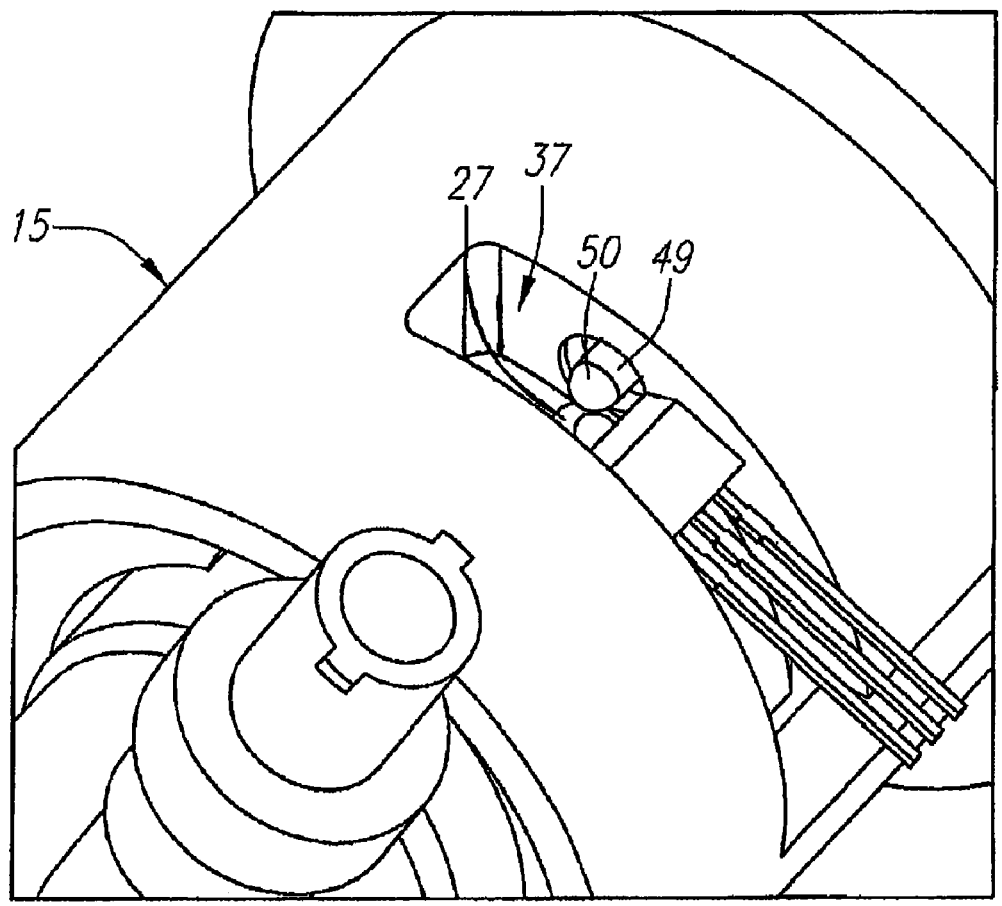
FIG. 9 is a blowup view of the catheter turned further clockwise in the lock receptacle so that the indexing pin pushes down on the plunger according to an embodiment.
Figure 10:
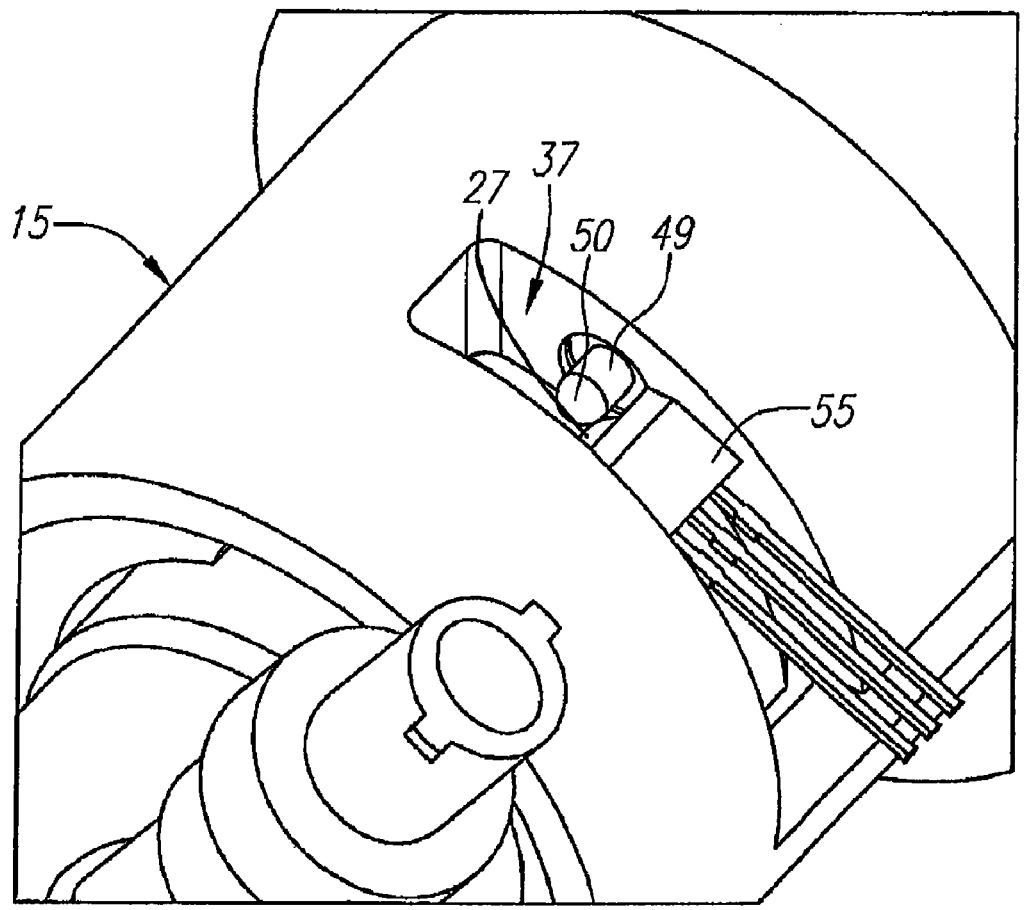
FIG. 10 is a blowup view of the catheter turned further clockwise in the lock receptacle to a locked position according to an embodiment.

The catheter 10 is then twisted or turned clockwise. As the catheter 10 is turned clockwise, the indexing pin 27 contacts the ball-shaped end 50 of the ball plunger 49, as shown in FIG. 8. As the catheter 10 is turned further, the indexing pin 27 pushes down on the ball-shaped end 50 of the plunger 49 allowing the indexing pin 27 to move passed the plunger 49, as shown in FIG. 9. The force of the plunger 49 provides the user with a tactile feel of locking. After the indexing pin 27 passes the plunger 49, the plunger 49 pops up behind the indexing pin 27 and the indexing pin 27 engages the retaining wall 40 of the radial slot 37, as shown in FIG. 10. Although the view of the retaining wall 40 is obscured by the sensor 55 in FIG. 10, the retaining wall can be seen in FIG. 4. In this position, the indexing pin 27 is locked between the plunger 49 and the retaining wall 40, and is therefore in the locked position. In addition, the magnet 30 on the indexing pin 27 is aligned with the Hall-effect sensor 55. In the locked position, the Hall-effect sensor 55 detects the presence of the magnet 30, and hence the catheter 10 in the locked position. The Hall-effect sensor 55 sends a signal to the protection circuitry 60 indicating that the catheter 10 is locked in the locking receptacle 15. In response, the protection circuitry 60 enables the motor 62 of the motor drive unit.

When the Hall-effect sensor 55 does not detect the presence of the magnet 30 of the indexing pin 27, the protection circuitry 60 disables the motor 62 of the motor drive unit to prevent the motor 62 from switching on when the catheter is not connected to the motor drive unit. This prevents accidental injury of a person inserting his/her finger into the locking receptacle 15 while the motor running.

To lock the catheter 10 in the lock receptacle 15, the catheter 10 is preferably turned 15 degrees clockwise in the lock receptacle 15. In FIG. 10, vertical line 80 shows the initial direction of the indexing pin 27 and line 85 shows the direction of the indexing pin 27 in the locked position. The angel between the lines 80 and 85 is 15 degrees. Although, the catheter 10 is turned 15 degrees clockwise in the preferred embodiment, the catheter 10 may be turned counterclockwise and/or turned a different degree, e.g., 45 degrees.

Figure 11:
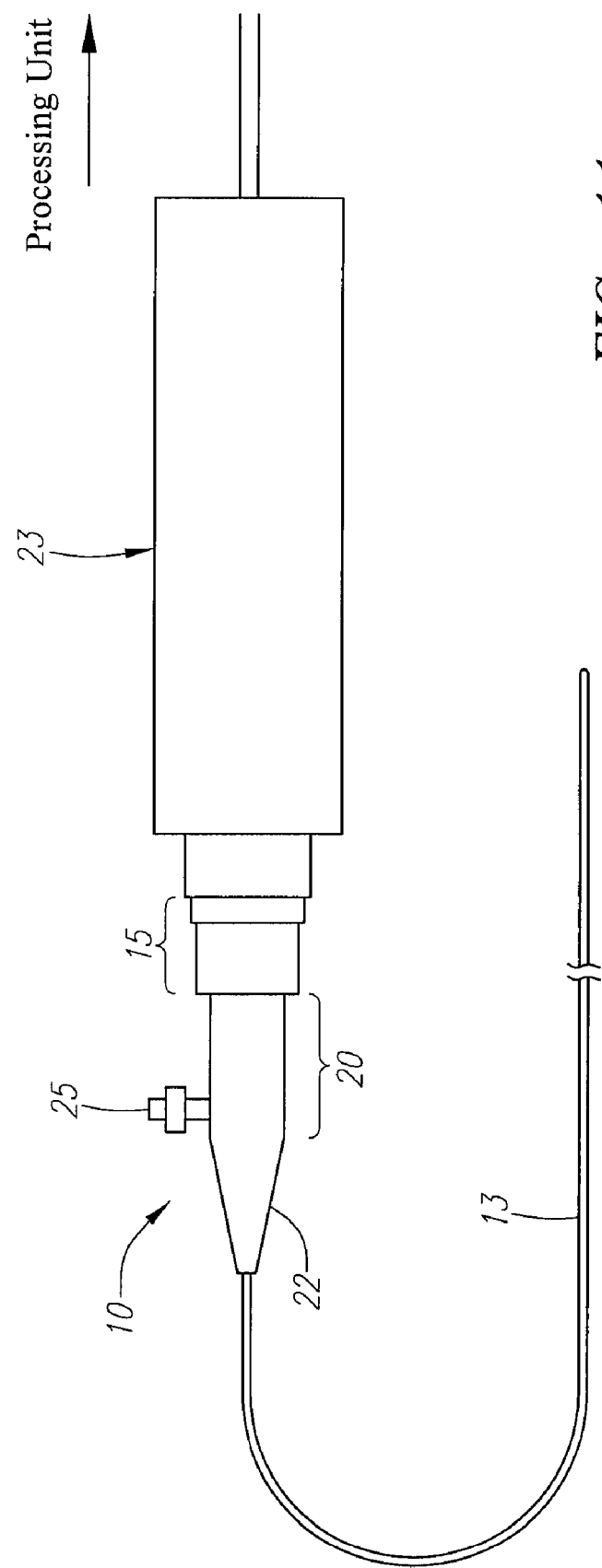
FIG. 11 shows a catheter locked to an exemplary motor drive unit by the lock receptacle according to an embodiment.

FIG. 11 shows the catheter 10 locked to an exemplary motor drive unit 23 by the lock receptacle 15. As shown in FIG. 11, the catheter 10 includes an elongated catheter body 13 configured to be inserted into a patient's body, e.g., through a blood vessel. The catheter 10 may include an ultrasound transducer (not shown) attached to the distal tip of a drive cable (not shown), both of which are rotatable within the catheter body 13. The drive cable is mechanically coupled to a drive motor (not shown) within the motor drive unit 23 for rotating the drive cable and the ultrasound transducer within the catheter body 23 to obtain images within the patient's body. Signals from the transducer pass through the motor drive unit 23 to a processing unit (not shown).

In another embodiment, the indexing pin may include two or more magnets at different positions on the indexing pin to enable the recognition of different catheters. In this embodiment, the lock receptacle includes multiple Hall-effect sensors at different positions configured to detect the presence of magnets at different positions on the indexing pin when the catheter is locked in. Different catheters may have magnets at different positions on the indexing pin enabling catheter recognition circuitry coupled to the Hall-effect sensors to detect the different catheters based on which of the Hall-effect sensors detect a magnet. Therefore, multiple magnets can be used to define signatures for different catheters, and thus create a catheter recognition system with the use of simple magnets instead of complicated circuitry.

Although the preferred embodiment was described in the context of a motor drive unit and a rotating imaging transducer, the present invention is not so limited and may be used in other applications in which locking and detecting the presence of a catheter is desirable. For example, instead of a rotating imaging transducer, a surgical tool or other type of device may be attached to the distal end of the drive cable. Further, the proximal end of the catheter may be locked to another type of system besides a motor drive unit in which detecting the presence of the catheter connected to the system is useful.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A catheter system, comprising:
  a catheter having a proximal end;
  a magnet attached to the proximal end of the catheter;
  a lock receptacle configured to receive and lock the proximal end of the catheter therein; and
  a Hall-effect sensor configured to detect the presence of the magnet when the proximal end of the catheter is locked in the lock receptacle.

2. The catheter system of claim 1, further comprising:
  protection circuitry coupled to the Hall-effect sensor; and
  a motor coupled to the protection circuitry, wherein the protection circuitry is configured to disable the motor when the Hall-effect sensor does not detect the presence of the magnet.

3. The catheter system of claim 1, further comprising an indexing pin extending radially from the proximal end of the catheter, wherein the magnet is attached to the indexing pin.

4. The catheter system of claim 3, wherein the lock receptacle further comprises:
  a radial groove configured to receive the indexing pin therein; and
  a plunger extending from a side wall of the radial groove, wherein the plunger is configured to lock the indexing pin between the plunger and a retaining wall of the radial groove.

5. The catheter of claim 4, wherein the Hall-effect sensor is configured to detect the magnet when the indexing pin is locked between the plunger and the retaining wall.

6. The catheter system of claim 5, further comprising:
  protection circuitry coupled to the Hall-effect sensor; and
  a motor coupled to the protection circuitry, wherein the protection circuitry is configured to disable the motor when the Hall-effect sensor does not detect the presence of the magnet.

7. The catheter system of claim 4, wherein the plunger is spring loaded.

8. The catheter system of claim 4, wherein the plunger has a ball-shaped tip.

9. The catheter system of claim 4, wherein the lock receptacle further comprises an inner cavity configured to receive the proximal end of the catheter therein, and an axial groove within the inner cavity connected to the radial groove, wherein the axial groove is configured to allow the indexing pin to pass there through to be received in the radial groove.

10. The catheter system of claim 9, wherein the plunger is configured to lock the indexing pin when the indexing pin is rotated between 15 and 45 degrees within the radial groove.

11. The catheter system of claim 1, further comprising:
  multiple magnets at different positions on the proximal end of the catheter; and
  multiple Hall-effect sensors, wherein each Hall-effect sensor is configured to detect a different one of the magnets when the proximal end of the catheter is locked in the lock receptacle.

12. The catheter system of claim 1, wherein the lock receptacle is made of a non-conductive material.

13. The catheter system of claim 1, wherein the magnet is a neodymium magnet.

14. The catheter system of claim 1, wherein the catheter system comprises a plurality of magnets at different positions on the indexing pin.

15. A system comprising:
  a catheter system comprising
    an elongated catheter body having a proximal end,
    an imaging transducer disposed in the catheter body,
    a lock receptacle configured to receive and lock the proximal end of the catheter therein;
    a magnet disposed on a portion of the catheter system; and
    a Hall-effect sensor disposed on a portion of the catheter system;
    wherein the catheter system is configured and arranged so that locking the proximal end of the catheter in the lock receptacle aligns the magnet with the Hall-effect sensor;
  a motor drive unit coupled to the catheter system; and
  a processing unit coupled to the catheter system and configured and arranged for receiving signals from the imaging transducer.

16. The system of claim 15, wherein the catheter further comprises a drive cable coupled to the imaging transducer to rotate the imaging transducer within the catheter body.

17. A catheter system, comprising:
  a catheter having a proximal end;
  a lock receptacle configured to receive and lock the proximal end of the catheter therein;
  a magnet disposed on a portion of the catheter system; and
  a Hall-effect sensor disposed on a portion of the catheter system;
  wherein the catheter system is configured and arranged so that locking the proximal end of the catheter in the lock receptacle aligns the magnet with the Hall-effect sensor.

18. The catheter system of claim 17, further comprising an indexing pin extending radially from the proximal end of the catheter.

19. The catheter system of claim 18, wherein the lock receptacle further comprises a radial groove configured to receive the indexing pin therein.

20. The catheter system of claim 19, wherein the lock receptacle further comprises a plunger extending from a side wall of the radial groove, wherein the plunger is configured to lock the indexing pin between the plunger and a retaining wall of the radial groove.

* * * * *